(12) United States Patent
Langlois et al.

(10) Patent No.: US 10,383,935 B2
(45) Date of Patent: Aug. 20, 2019

(54) METHODS OF MAKING AND USING LIVE ATTENUATED VIRUSES

(71) Applicant: Regents of the University of Minnesota, Minneapolis, MN (US)

(72) Inventors: Ryan Andrew Langlois, Minneapolis, MN (US); Jessica Karen Fiege, Minneapolis, MN (US); Louisa Elizabeth Sjaastad, Minneapolis, MN (US); Barbara Mae Waring, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/799,465

(22) Filed: Oct. 31, 2017

(65) Prior Publication Data

US 2018/0177863 A1    Jun. 28, 2018

Related U.S. Application Data

(63) Continuation-in-part of application No. 15/274,491, filed on Sep. 23, 2016.

(60) Provisional application No. 62/222,322, filed on Sep. 23, 2015.

(51) Int. Cl.
| | | |
|---|---|---|
| *C07H 21/02* | (2006.01) | |
| *C07H 21/04* | (2006.01) | |
| *A61K 39/145* | (2006.01) | |
| *C12N 7/00* | (2006.01) | |
| *C12N 5/071* | (2010.01) | |
| *C12N 15/113* | (2010.01) | |
| *A61K 39/12* | (2006.01) | |
| *A61K 39/00* | (2006.01) | |
| *A61P 31/16* | (2006.01) | |

(52) U.S. Cl.
CPC ............ *A61K 39/145* (2013.01); *A61K 39/12* (2013.01); *C12N 5/0686* (2013.01); *C12N 7/00* (2013.01); *C12N 15/113* (2013.01); *A61K 2039/5254* (2013.01); *A61K 2039/575* (2013.01); *A61P 31/16* (2018.01); *C12N 2310/113* (2013.01); *C12N 2310/141* (2013.01); *C12N 2310/20* (2017.05); *C12N 2501/65* (2013.01); *C12N 2760/16021* (2013.01); *C12N 2760/16034* (2013.01); *C12N 2760/16162* (2013.01)

(58) Field of Classification Search
CPC .......................... C12N 2310/11; C12N 15/113
See application file for complete search history.

(56) References Cited

U.S. PATENT DOCUMENTS

| | | |
|---|---|---|
| 5,453,566 A | 9/1995 | Shewmaker et al. |
| 6,107,094 A | 8/2000 | Crooke |
| 6,506,559 B1 | 1/2003 | Fire et al. |
| 7,056,704 B2 | 6/2006 | Tuschl et al. |
| 7,078,196 B2 | 7/2006 | Tuschl et al. |
| 8,883,995 B2 | 11/2014 | tenOever |

FOREIGN PATENT DOCUMENTS

| | | | | |
|---|---|---|---|---|
| EP | 2403527 | | 1/2012 | |
| WO | WO 2005/056761 A2 | * | 6/2005 | ........... C12N 15/113 |
| WO | WO 2010/101663 | | 9/2010 | |
| WO | WO 2013/102155 | | 7/2013 | |
| WO | WO 2014/159633 A1 | * | 10/2014 | ......... C12N 2310/11 |

OTHER PUBLICATIONS

Chuang et al. (Cancer Research, 59, 3073-3076, 1999).*
McDonald et al. (Journal of the American College of Cardiology, vol. 65, No. 21, Jun. 2015, pp. 2314-2327).*
Barnes et al., "Harnessing endogenous miRNAs to control virus tissue tropism as a strategy for developing attenuated virusvaccines," *Cell Host Microbe.*, 4(3):239-48, Sep. 11, 2008.
Bartel, "MicroRNA Target Recognition and Regulatory Functions," *Cell.*, 136(2):215-233, Jan. 23, 2009.
Chenna et al., "Multiple sequence alignment with the Clustal series of program," *Nucleic Acids Res.*, 31(13):3497-3500, 2003.
GenBank Accession No. NR_029493, "*Homo sapiens* microRNA 21 (MIR21), microRNA," May 14, 2014, 3 pages.
GenBank Accession No. NR_029738, "*Mus musculus* microRNA 21a (Mir21a), microRNA," May 26, 2014, 3 pages.
GenBank Accession No. NR_030880, "*Bos taurus* microRNA mir-21 (MIR21), microRNA," Dec. 11, 2014, 2 pages.
GenBank Accession No. NR_031583, "*Gallus gallus* microRNA 21 (MIR21), microRNA," Sep. 3, 2014, 2 pages.
GenBank Accession No. NR_031823, "*Rattus norvegicus* microRNA 21 (Mir21), microRNA," Sep. 4, 2014, 3 pages.
GenBank Accession No. NR_031992, "*Macaca mulatta* microRNA mir-21 (MIR21), microRNA," Jul. 16, 2013, 2 pages.
GenBank Accession No. NR_031993, "*Pan troglodytes* microRNA mir-21 (MIR21), microRNA," Jul. 17, 2013, 2 pages.
GenBank Accession No. NR_032904, "*Equus caballus* microRNA mir-21 (MIR21), microRNA," Dec. 11, 2014, 2 pages.
GenBank Accession No. NR_038508, "*Sus scrofa* microRNA mir-21 (MIR21), microRNA," Dec. 11, 2014, 3 pages.
GenBank Accession No. NR_045131, "*Cricetulus griseus* microRNA mir-21 (Mir21), microRNA," Nov. 19, 2013, 2 pages.
GenBank Accession No. NR_049391, "*Canis lupus familiaris* microRNA mir-21 (MIR21), microRNA," Dec. 11, 2014, 2 pages.

(Continued)

*Primary Examiner* — Amy H Bowman
(74) *Attorney, Agent, or Firm* — Fish & Richardson P.C.

(57) ABSTRACT

This disclosure provides live, attenuated viruses, and methods of making and using the live, attenuated viruses.

5 Claims, 10 Drawing Sheets
Specification includes a Sequence Listing.

(56) References Cited

OTHER PUBLICATIONS

GenBank Accession No. NR_106222, "Gorilla gorilla microRNA mir-21 (MIR21), microRNA," Dec. 10, 2014, 2 pages.
GenBank Accession No. NR_107879, "Ovis aries microRNA mir-21 (MIR21), microRNA," Dec. 11, 2014, 2 pages.
Kelly et al, "Engineering microRNA responsiveness to decrease virus pathogenicity," *Nature Medicine.*, 14(11):1278-1283, Nov. 2008.
Langlois et al., "In vivo delivery of cytoplasmic RNA virus-derived miRNAs," *Mol.Therapy.*, 20(2):367-375, Feb. 2012.
Langlois et al., "Hematopoietic-specific targeting of influenza A virus reveals replication requirements for induction of antiviral immune responses," *PNAS.*, 109(30): 12117-12122, Jul. 24, 2012.
Langlois et al., "MicroRNA-based strategy to mitigate the risk of gain-of-function influenza studies," *Nature Biotechnology.*, 31(9):844-847, Aug. 11, 2013.
Perez et al., "MicroRNA-mediated species-specific attenuation of influenza A virus," *Nature Biotechnology.*, 27:572-576, 2009.
Pfeffer et al., "Identification of microRNAs of the herpesvirus family," *Nat Methods.*, 2(4):269-276, 2005.
Pham et al., "Replication in Cells of Hematopoietic Origin Is Necessary for Dengue Virus Dissemination," *PLoS Pathogens.*, 8(1):e1002465, 10 pages, Jan. 5, 2012.
Shapiro et al., "Noncanonical cytoplasmic processing of viral microRNAs," *RNA.*, 16(11):2068-2074, Nov. 2010.
U.S. Appl. No. 15/274,491, filed Sep. 23, 2016, 20170080079, Mar. 23, 2017, Langlois et al.

\* cited by examiner

SEQUENCE LISTING

```
<160> NUMBER OF SEQ ID NOS: 14

<210> SEQ ID NO 1
<211> LENGTH: 22
<212> TYPE: RNA
<213> ORGANISM: Homo sapiens

<400> SEQUENCE: 1
cgcauuauua cucacgguac ga                                              22

<210> SEQ ID NO 2
<211> LENGTH: 21
<212> TYPE: RNA
<213> ORGANISM: Homo sapiens

<400> SEQUENCE: 2
acuagacugu gagcuccucg a                                               21

<210> SEQ ID NO 3
<211> LENGTH: 23
<212> TYPE: DNA
<213> ORGANISM: Homo sapiens

<400> SEQUENCE: 3
tccataaagt aggaaacact aca                                             23

<210> SEQ ID NO 4
<211> LENGTH: 22
<212> TYPE: DNA
<213> ORGANISM: Homo sapiens

<400> SEQUENCE: 4
tcaacatcag tctgataagc ta                                              22

<210> SEQ ID NO 5
<211> LENGTH: 21
<212> TYPE: DNA
<213> ORGANISM: Homo sapiens

<400> SEQUENCE: 5
gcaagctgac cctgaagttc a                                               21

<210> SEQ ID NO 6
<211> LENGTH: 20
<212> TYPE: DNA
```

```
<213> ORGANISM: Artificial
<220> FEATURE:
<223> OTHER INFORMATION: Synthetic oligonucleotide

<400> SEQUENCE: 6
tgataagcta cccgacaagg                                           20

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide

<400> SEQUENCE: 7
atcccaaagt caaacctagt                                           20

<210> SEQ ID NO 8
<211> LENGTH: 23
<212> TYPE: DNA
<213> ORGANISM: Artificial
<220> FEATURE:
<223> OTHER INFORMATION: Synthetic oligonucleotide

<400> SEQUENCE: 8
ggttggtgtc tcatgaatga gct                                       23

<210> SEQ ID NO 9
<211> LENGTH: 25
<212> TYPE: DNA
<213> ORGANISM: Artificial
<220> FEATURE:
<223> OTHER INFORMATION: Synthetic oligonucleotide

<400> SEQUENCE: 9
ccacgaaaat ttaaggcaca aaatg                                     25

<210> SEQ ID NO 10
<211> LENGTH: 22
<212> TYPE: DNA
<213> ORGANISM: Artificial
<220> FEATURE:
<223> OTHER INFORMATION: Synthetic oligonucleotide

<400> SEQUENCE: 10
tcaacatcag tctgataagc ta                                        22

<210> SEQ ID NO 11
<211> LENGTH: 22
<212> TYPE: DNA
<213> ORGANISM: Artificial
<220> FEATURE:
<223> OTHER INFORMATION: Synthetic oligonucleotide

<400> SEQUENCE: 11
taaccgattt cagatggtgc ta                                        22

<210> SEQ ID NO 12
<211> LENGTH: 23
<212> TYPE: DNA
<213> ORGANISM: Artificial
<220> FEATURE:
<223> OTHER INFORMATION: Synthetic oligonucleotide

<400> SEQUENCE: 12
gccatgctaa tcttctctgt atc                                       23
```

```
<210> SEQ ID NO 13
<211> LENGTH: 72
<212> TYPE: DNA
<213> ORGANISM: Homo sapiens

<400> SEQUENCE: 13
tgtcgggtag cttatcagac tgatgttgac tgttgaatct catggcaaca ccagtcgatg        60
ggctgtctga ca                                                            72

<210> SEQ ID NO 14
<211> LENGTH: 22
<212> TYPE: DNA
<213> ORGANISM: Homo sapiens

<400> SEQUENCE: 14
tcaacatcag tctgataagc ta                                                 22
```

METHODS OF MAKING AND USING LIVE ATTENUATED VIRUSES

CROSS REFERENCE TO RELATED APPLICATIONS

This application is a Continuation-In-Part of, and claims the benefit of priority under 35 U.S.C. § 120 to, U.S. application Ser. No. 15/274,491 filed Sep. 23, 2016, which claims the benefit of priority under 35 U.S.C. § 119(e) to U.S. Application No. 62/222,322 filed Sep. 23, 2015.

TECHNICAL FIELD

This disclosure generally relates to live attenuated viruses and materials and methods for making such live attenuated viruses.

BACKGROUND

An attenuated vaccine is a live vaccine, which can be contrasted with a killed vaccine. An attenuated vaccine is created by reducing the virulence of a pathogen, or eliminating the virulence of a pathogen under certain conditions. Live attenuated vaccines provide better protection to the host, but safety concerns have limited their use outside of the human population. These concerns are obviated by the materials and methods described herein.

SUMMARY

The methods described herein provide a new platform that includes a cell line deficient in one or more universally expressed miRNAs. The platform described herein allows for the production of live, miRNA-attenuated vaccines that can be safely used, for example, in mammalian and avian species.

In one aspect, a miRNA-21 knockout cell line is provided. Such a cell line typically includes one or more mutations in the endogenous miRNA-21 nucleic acid sequence. In some embodiments, the cell line is a eukaryotic cell line (e.g., a Madin-Darby Canine Kidney (MDCK) cell line). In some embodiments, the miRNA-21 has the sequence shown in SEQ ID NO:13. In some embodiments, the one or more mutations are selected from the group consisting of a deletion, an insertion, a point mutation, or a substitution. A representative miRNA-21 knockout cell line is deposited with the ATCC under Accession No. PTA-125918.

In another aspect, a live, attenuated influenza virus is provided. Such a live, attenuated influenza virus typically includes at least one miRNA-21 recognition nucleic acid sequence. In some embodiments, the influenza virus is selected from the group consisting of influenza A, influenza B, and influenza C. In some embodiments, the influenza virus is influenza A H2N2. In some embodiments, the miRNA-21 recognition nucleic acid sequence has the sequence shown in SEQ ID NO:14. In some embodiments, the miRNA-21 recognition nucleic acid sequence is introduced in or near the nucleoprotein (NP) gene. In some embodiments, the virus further comprises at least one additional miRNA recognition nucleic acid sequence that is not miRNA-21.

In one aspect, a method of making a live, attenuated virus is provided. Such a method generally includes providing a modified virus, wherein the virus has been modified to comprise a miRNA-recognition nucleic acid sequence; culturing the modified virus in a miRNA knock-out cell line, wherein the knock-out cell line comprises a mutation or a transgene that results in the absence of the miRNA that, when present, binds to the miRNA-recognition nucleic acid sequence; and collecting the cultured virus, wherein the cultured virus is annotated when introduced into a cell expressing the miRNA.

Representative miRNAs include, without limitation, miRNA-23, miRNA-24, miRNA-29, miRNA-103, and miRNA-107. Representative viruses include, without limitation, an Influenza B virus, respiratory syncytial virus (RSV), polio virus, West Nile virus, Chikungunya virus, Ebola virus, Lassa virus, Dengue virus, SARS coronavirus, and Middle East Respiratory Syndrome (MERS) coronavirus.

In some embodiments, the modified virus includes one miRNA-recognition nucleic acid sequence. In some embodiments, the modified virus includes a plurality of miRNA-recognition nucleic acid sequences.

In some embodiments, the mutation is an insertion, a deletion, a substitution, or a point mutation. In some embodiments, the transgene encodes at least one inhibitory nucleic acid (e.g., an antisense RNA, a RNAi, or a siRNA).

In another aspect, a live, attenuated virus is provided. In one embodiment, a live, attenuated virus made by the methods described herein is provided. In one embodiment, a live, attenuated virus is provided that includes a miRNA-recognition nucleic acid sequence in its genome.

In still another aspect, a method of vaccinating a subject is provided. Such a method generally includes inoculating the subject with a live, attenuated virus as described herein. Representative subjects include, without limitation, humans, birds, cows, pigs, ferrets, dogs, or cats.

In yet another aspect, an article of manufacture is provided that includes a live, attenuated virus as described herein. In some embodiments, the article of manufacture further includes a knock-out cell line as described herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A—microRNA-Based Platform to Generate Live Viruses Attenuated Across Species

Figure 4:
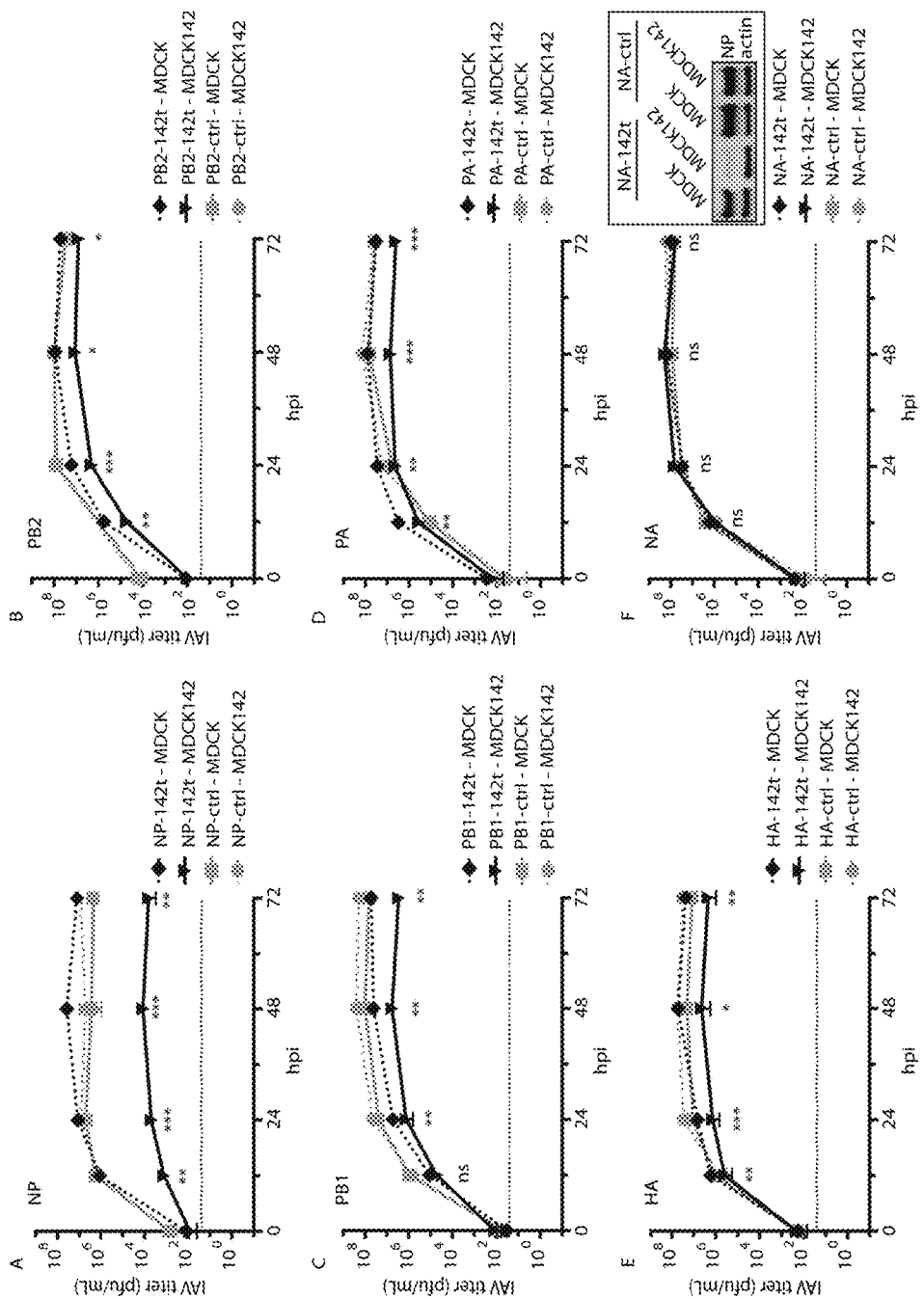

Part B—microRNA-21-Based Attenuation of Influenza Virus Across Susceptible Hosts FIG. 4 are graphs showing miRNA targeting of IAV NP mRNA most effectively ablates viral replication. MDCK and MDCK 142 cells were infected at a MOI of 0.02 and virus titered from supernatant at the indicated times post-infection in MDCK cells using the following miR-142 targeted viruses and their corresponding controls: Panel A is NP-142t and NP-ctrl; Panel B is PB2-142t and PB2-ctrl; Panel C is PB1-142t and PB1-ctrl; Panel D is PA-142t and PA-ctrl; Panel E is HA-142t and HA-ctrl; and Panel F is NA-142t and NA-ctrl. Inset shows MDCK and MDCK142 cells infected with NA-142t and NA-ctrl at a MOI 0.5 and Western Blot analysis for NA and actin. Dotted line represents limit of detection. Data points at the indicated times were performed in triplicate; error bars represent standard deviation. *$p \leq 0.001$, $p \leq 0.01$, *$p \leq 0.05$. Data are representative of two independent experiments.

Figure 5:
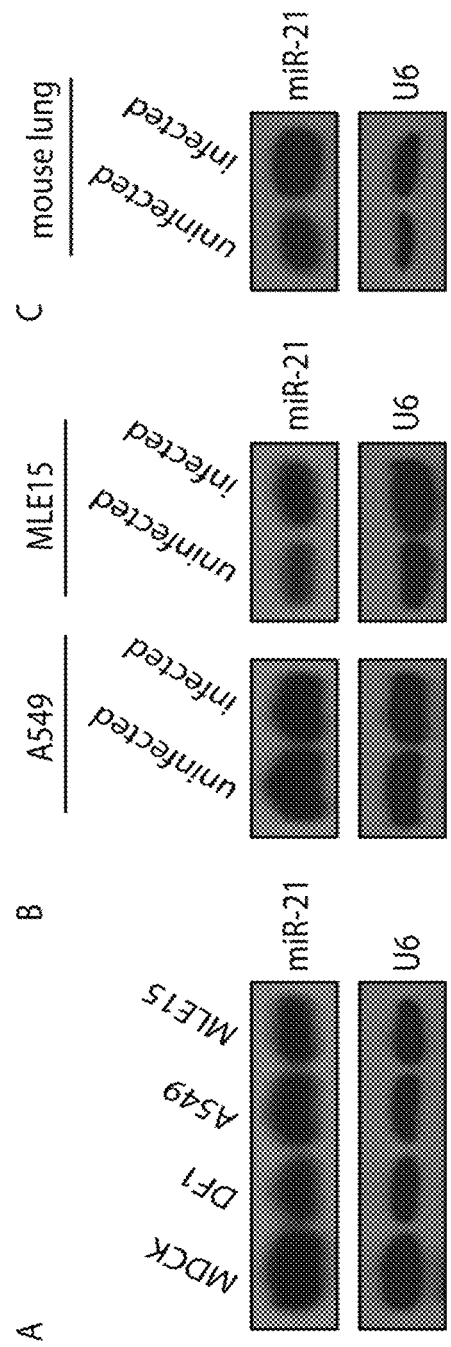

FIG. 5 are photographs of gels showing that miR-21 is abundantly expressed in IAV-susceptible hosts. Small RNA Northern blot analysis was performed to analyze expression of miR-21, miR-29 and U6 in MDCK, DF-1, A549, MLE15 cells (Panel A), A549 and MLE cells infected with PR8 at a MOI of 1 (Panel B), and lungs of a naive mouse and a mouse infected with 40 pfu of PR8 (Panel C).

Figure 6:
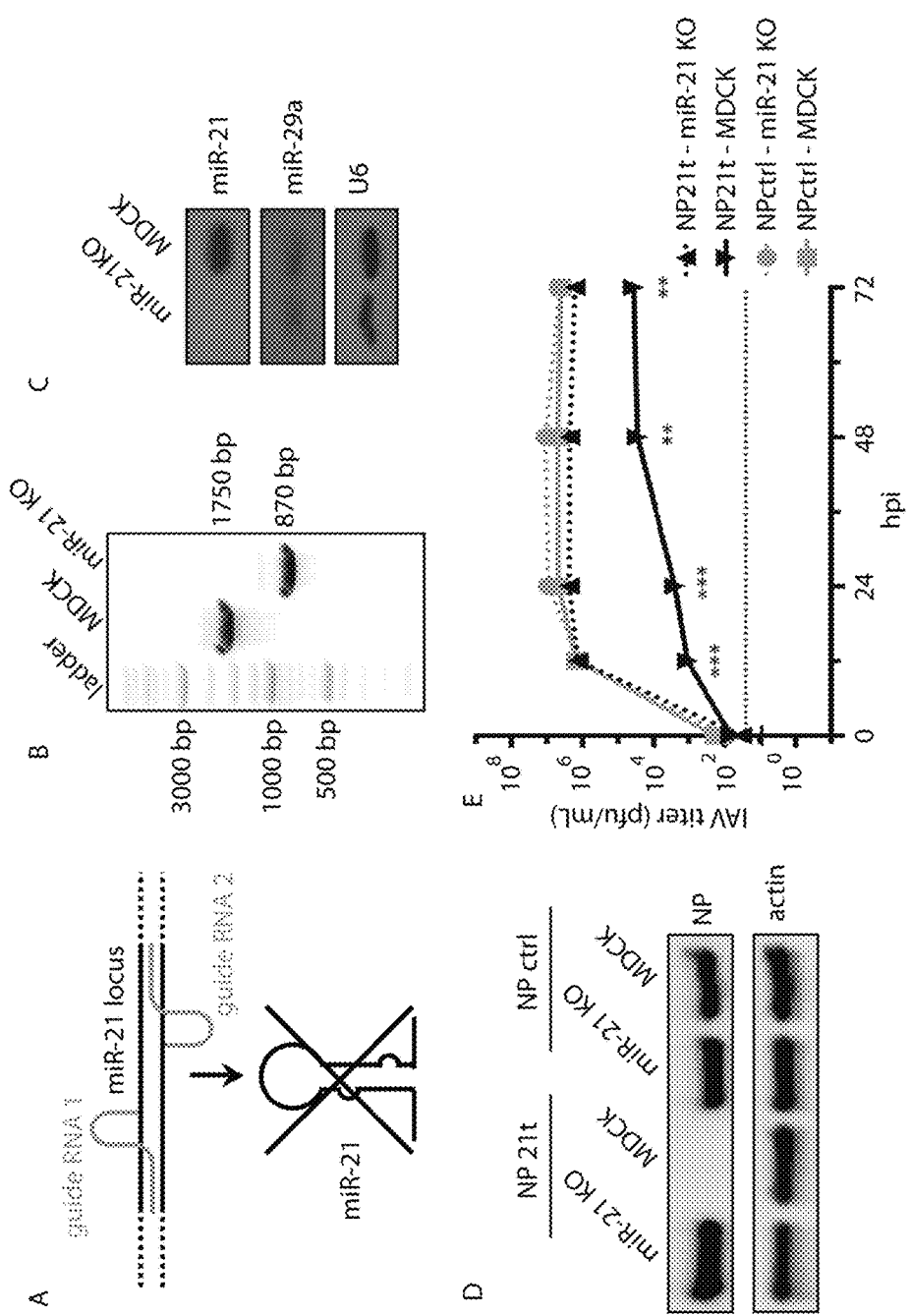

FIG. 6 are images showing the generation of miR-21-knockout MDCK cells. Panel A is a schematic model demonstrating use of dual guide RNAs to eliminate the entire primary miR-21 locus. Panel B is a photograph of agarose gel electrophoresis of genomic PCR products spanning miR-21 from unmodified and miR-21 KO MDCK cells. Panel C is photographs of Northern blot analysis for miR-21 (upper), miR-29 (middle), and U6 (lower) RNA in MDCK and miR-21 KO cells. Panel D is photographs of gels showing Western blot analysis of MDCK and miR-21 KO cells infected with NP-21t or NP-ctrl virus at an MOI of 0.5 to determine abundance of viral NP (upper); actin (lower) is shown as a loading control. Panel E is a graph showing multicycle infections performed at a MOI of 0.02 and virus titered from supernatant at the indicated times post infection in miR-21 KO cells in triplicate: error bars represent standard deviation. Dotted line represents limit of detection. *$p \leq 0.001$, $p \leq 0.01$, *$p \leq 0.05$. Data are representative of two independent experiments.

Figure 7:
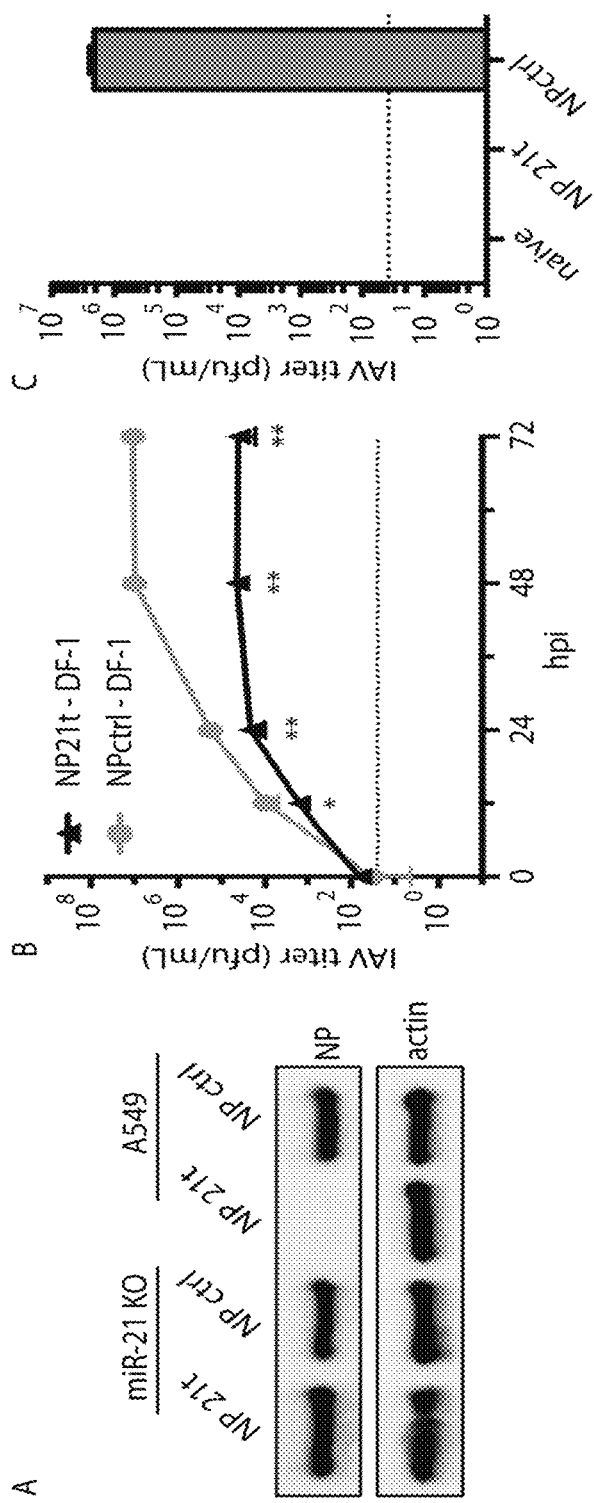

FIG. 7 is experimental data showing that miR-21 targeted virus is attenuated in influenza-susceptible hosts. Panel A is photographs of miR-21 KO MDCK and A549 cells infected at an MOI of 0.5 with NP-21t or NP-ctrl virus for a single cycle of replication. Viral NP (upper) abundance was determined by Western blot; actin (lower) is shown as a loading control. Panel B is a graph showing multicycle infections performed in DF-1 cells infected at a MOI 0.02 with indicated viruses in triplicate. Panel C is a graph showing mice infected with 100 pfu of NP-21t or NP-ctrl virus i.n. and virus was titered from whole lung homogenate at 3 dpi (n=5 NP-21t, 5 NP-ctrl, 1 Naïve mice per group). Dotted line represents limit of detection. Error bars represent standard deviation. *$p \leq 0.001$, $p \leq 0.01$, *$p \leq 0.05$. Data are representative of two independent experiments.

Figure 8:
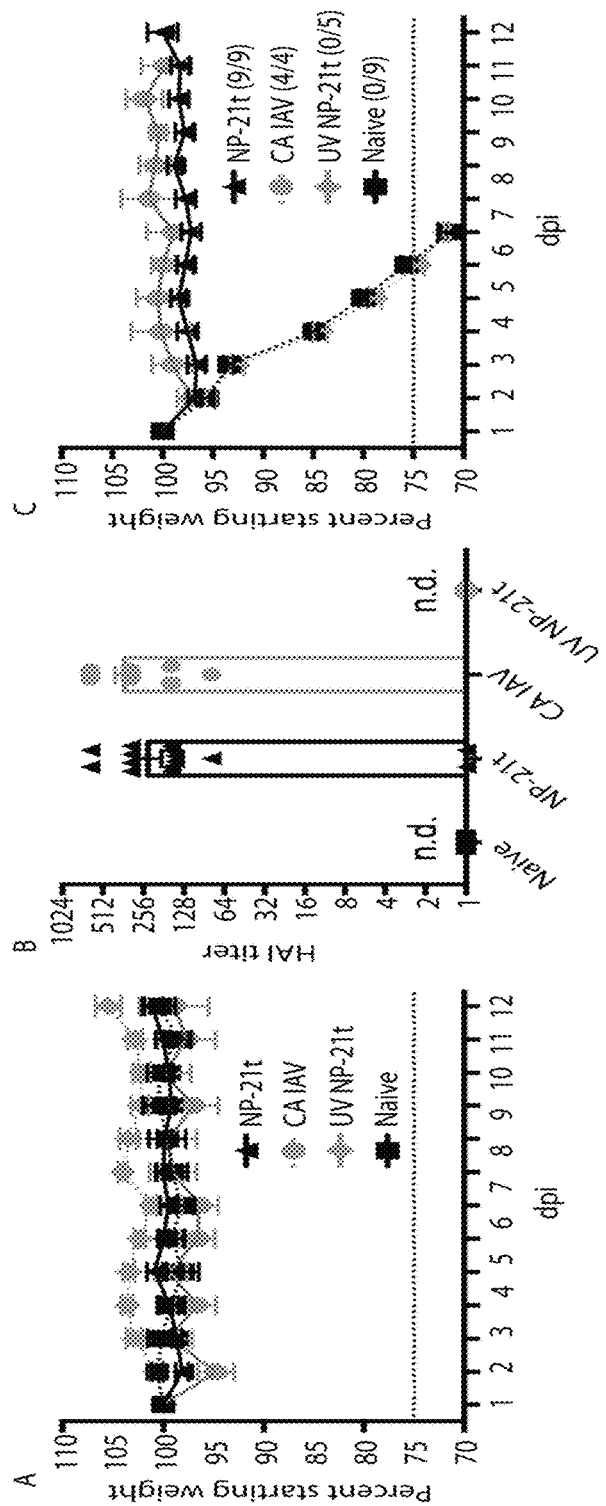

FIG. 8 are graphs showing that vaccination with NP-21t virus confers protection during secondary IAV infection. Mice were infected with 100 pfu of NP-21t, 100 pfu of UV-killed NP21t, or 1000 pfu of Cold Adapted IAV (CA IAV) i.n. (n=9 NP-21t, 5 UV NP-21t, 4 CA IAV, and 9 naïve mice per group) and percent initial weight (Panel A) was assessed at the indicated dpi. Panel B is a graph showing 28 dpi serum analyzed for HA-specific antibodies by HA inhibition assay (n=15 NP-21t, 9 UV NP-21t, 11 CA IAV, and 13 naïve mice per group). At 29 dpi, mice were challenged with a lethal dose (1000 pfu) of PR8 virus. Panel C is a graph showing that weight loss and mortality were assessed at the indicated dpi (surviving mice per total infected are indicated in the parentheses).

Figure 9:
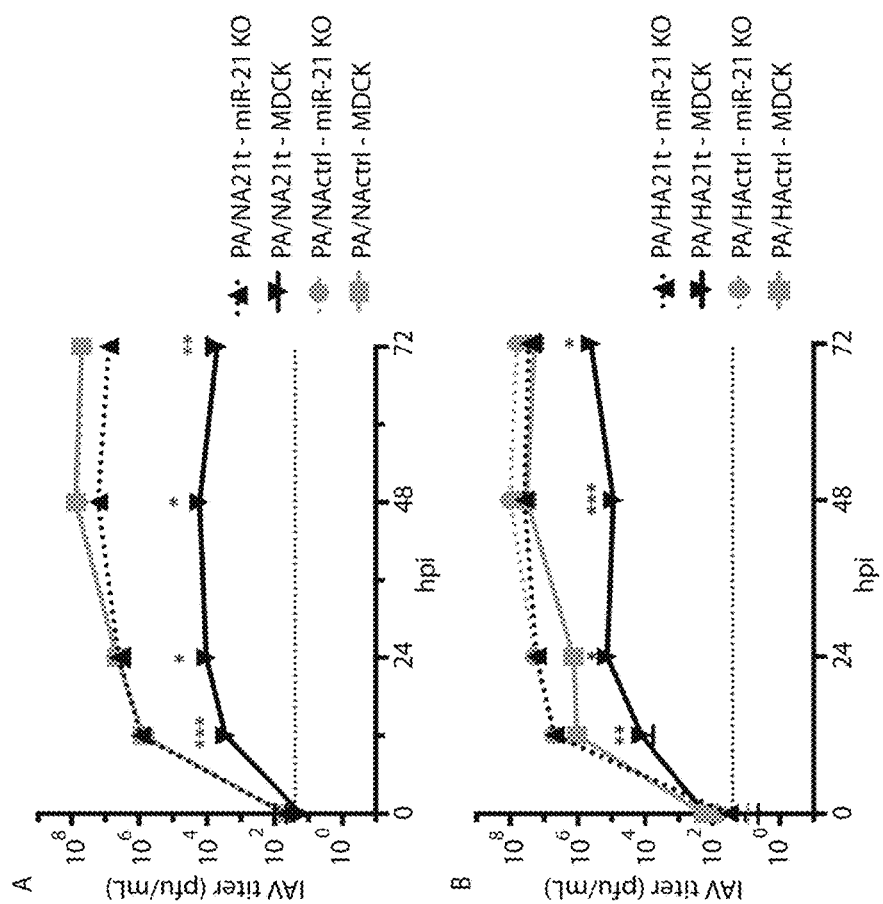

FIG. 9 are graphs showing the miRNA targeting of multiple gene segments. Multicycle infections for PA/NA (Panel A) and PA/HA (Panel B) double targeted viruses were performed in MDCK and miR-21 KO MDCK cells at a MOI of 0.02 and virus titered from supernatant at the indicated times post infection in miR-21 KO cells. Dotted line represents limit of detection. Data points at the indicated times were performed in triplicate: error bars represent standard deviation. *$p \leq 0.001$, $p \leq 0.01$, *$p \leq 0.05$. Data are representative of two independent experiments.

DETAILED DESCRIPTION

Vaccines that rely upon live attenuated viruses generally provide better protection to the host and usually do not require booster vaccinations, but safety concerns have limited their use, with the exception of a few instances. The approach described herein is unique in that species-ubiquitous microRNAs can be eliminated from cell lines used to grow and rescue the virus, but the virus contains recognition sequences for miRNAs that are ubiquitously expressed in at-risk species (e.g., the species to be vaccinated). The safety concerns usually associated with the use of live attenuated viruses as vaccines are obviated by the methods described herein because miRNAs are used that are universally expressed, which allows for the use of live attenuated vaccines in animals (e.g., domestic poultry) that have previously been hampered by safety concerns with respect to consuming those animals by humans.

Previous efforts to use miRNAs to generate live attenuated vaccines have taken advantage of the natural disparity in expression that some miRNAs exhibit within vaccine production systems (e.g., chicken eggs or Madin-Darby Canine Kidney (MDCK) epithelial cells) and the desired vaccinated population (e.g., humans). These previous approaches have significant limitations, as there are no miRNAs that are absent from, for example, MDCK cells lines but present at levels abundant enough in humans, at-risk mammals (e.g., canines, swine, felines, cattle), and domesticated avian species to repress, or attenuate, virus replication. This disclosure demonstrates that eliminating a universally expressed miRNA from a cell line can facilitate the production of a targeted virus that is broadly attenuated in cells from a range of species including mice, canine, poultry and humans. Importantly, this targeted virus still provides robust protection from lethal virus challenge.

Figures 1A, 1B, 1C:
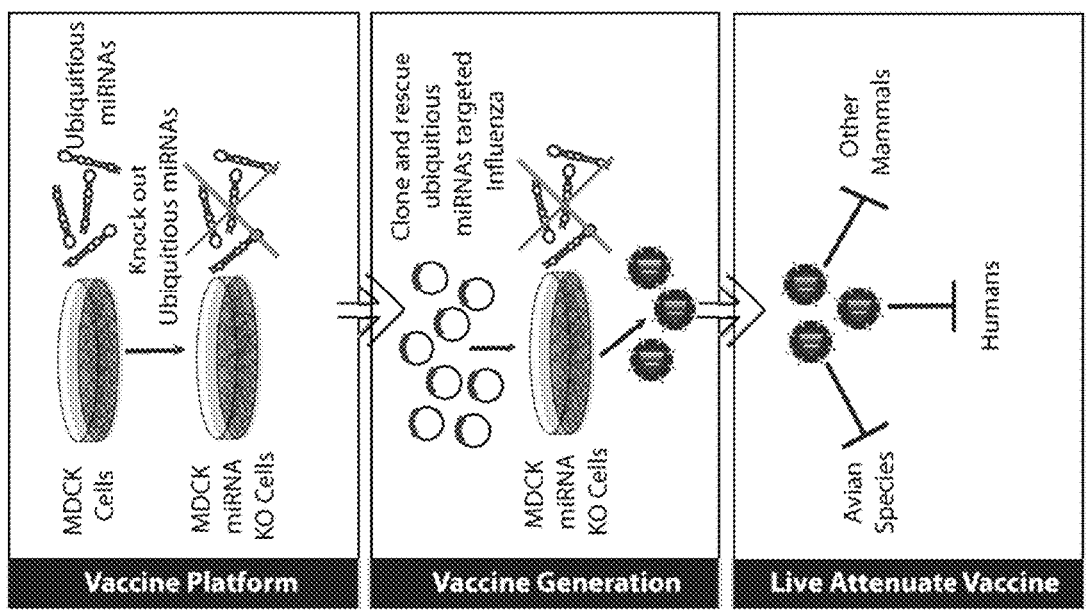
FIG. 1A is a schematic showing one embodiment of a miRNA-mediated vaccine platform as described herein.
FIG. 1B is a schematic showing one embodiment of vaccine generation as described herein.
FIG. 1C is a schematic showing the attenuated viruses that are produced by the methods described herein.

Methods are described herein that allow for recognition sequences for specific miRNAs to be engineered into the genomes of viruses, which can be used to restrict its replication in the presence of the cognate miRNA. FIG. 1 is a schematic showing one embodiment of a miRNA-mediated vaccine platform described herein. FIG. 1A shows that broadly expressed miRNAs can be knocked-out in a virus' host cell, and FIG. 1B is a schematic showing the subsequent generation of live, attenuated viruses, which can be used as vaccines. Specifically, FIG. 1B shows that a miRNA recognition sequence can be incorporated into the virus, and, using the miRNA-mediated vaccine platform shown in FIG. 1A, viral vaccines can be rescued and amplified. As shown in FIG. 1C, the resulting live vaccines are broadly attenuated in, for example, avian and mammalian species including humans.

The methods described herein are useful because they allow for generating live, attenuated viruses that can be used as vaccines in avian or mammalian species without the risk of spread into zoonotic hosts. For example, vaccination of turkeys or chickens with a live, attenuated virus as described herein will not result in infections of humans. In addition, since multiple segments of a virus can be targeted simultaneously, the possibility of reassortment of portions of the genome, which is a critical risk of current live, attenuated vaccine modalities, can be significantly diminished and even prevented by using the methods described herein.

miRNA Knockout Cell Line

A miRNA-mediated vaccine platform as described herein requires a cell line that has been engineered to be deficient in one or more miRNAs (e.g., a miRNA knock-out cell line). Such a cell line must be capable of supporting the life cycle of a virus and can be, for example, any number of eukaryotic cell types (e.g., mammalian cells (e.g., Madin-Darby Canine Kidney (MDCK) cells, African green monkey kidney cells (e.g., Vero), human embryonic retinal cells (e.g., PER.C6), human lung adenocarcinoma cells (e.g., A549), chick embryo cells (e.g., PBS-1), duck embryo retinal cells (AGE.CR), duck embryonic stem cells (e.g., EB66)) and/or insect cells (e.g., SF9)). To date, it has not been possible to generate a miRNA-targeted virus vaccine that is attenuated in both mammalian and avian species; the platform described herein allows for the development of such vaccines.

MicroRNAs are known in the art and are small (20-24 nt) regulatory non-coding RNAs that are involved in post-transcriptional regulation of gene expression in eukaryotes by affecting either or both the stability and translation of coding mRNAs. MicroRNAs are transcribed by RNA polymerase II as part of capped and polyadenylated primary transcripts ("pri-miRNAs") that can be protein-coding or non-protein-coding.

The primary transcript containing the miRNA is cleaved by the Drosha ribonuclease III enzyme to produce an approximately 70-nt stem-loop precursor miRNA ("pre-miRNA"), which is further cleaved by the cytoplasmic Dicer ribonuclease to generate the mature miRNA product and the "antisense miRNA asterisk" ("miRNA*") product, which generally is degraded. The mature miRNA is incorporated into a RNA-induced silencing complex (RISC), which recognizes target mRNAs through near perfect complimentary base pairing with the miRNA, which usually results in translational inhibition or destabilization of the target mRNA.

Representative miRNAs include, without limitation, miRNA-21, miRNA-23, miRNA-24, miRNA-29, miRNA-103, and/or miRNA-107. MicroRNAs are highly evolutionarily conserved within the animal kingdom and, in the miRNA-mediated vaccine platform described herein, it is desired that miRNAs that are expressed, e.g., abundantly expressed, e.g., ubiquitously expressed, in mammalian and/or avian species that are susceptible to the particular virus.

microRNA-21 (or "miR-21"), also known as hsa-mir-21, is a mammalian microRNA that is encoded by the MIR21 gene. The mature miR-21 sequence is strongly conserved throughout evolution. miRNA-21 sequences from a variety of organisms can be found, for example, at GenBank Accession Nos. NR_029493.1 (from *Homo sapiens*), NR_049391.1 (from *Canis lupus*), NR_032904.1 (from *Equus caballus*), NR_030880.1 (from *Bos taurus*), NR_031823.1 (from *Rattus norvegicus*), NR_031583.1 (from *Gallus gallus*), NR_029738.1 (from *Mus musculus*), NR_038508.1 (from *Sus scrofa*), NR_106222.1 (from *Gorilla gorilla*), NR_045131.1 (from *Cricetulus griseus*), NR_031993.1 (from *Pan troglodytes*), NR_031992.1 (from *Macaca mulatta*), and NR_107879.1 (from *Ovis aries*). The sequence of the stem-loop structure from the human miR-21 is shown below.

```
                                          (SEQ ID NO: 13)
TGTCGGGTAG CTTATCAGAC TGATGTTGAC TGTTGAATCT
CATGGCAACA CCAGTCGATG GGCTGTCTGA CA
```

Knock-out cell lines (i.e., cell lines deficient for one or more miRNAs) can be made using materials and methods well known in the art such as, without limitation, nucleases (e.g., CRISPR, TALENs, megaTALs, meganucleases, zinc finger nucleases); antibodies (e.g., Fab, Fab2, chimeric, humanized); or ligands, proteins, drugs, chemicals, or small molecules that competitively bind one or more miRNAs, that downregulate miRNA expression, that increase miRNA degradation, or that cause intracellular depletion (e.g., by secretion) of miRNA. See, for example, Sambrook et al., 1990, Molecular Cloning: A Laboratory Manual, Cold Spring Harbor, N.Y.

A skilled artisan also would appreciate that knock-out cell lines can be made, for example, using a transgene that encodes at least one inhibitory nucleic acid. Inhibitory nucleic acids are known in the art and can correspond to the sequence of the miRNA (e.g., a sense strand) or can be complementary to the sequence of the miRNA (e.g., an antisense strand). Inhibitory nucleic acids are known in the art and include, for example, antisense, RNAi, and siRNA. See, for example, U.S. Pat. Nos. 5,453,566; 6,107,094; 6,506,559; 7,056,704; and 7,078,196.

The use of inhibitory nucleic acids also is referred to as RNA interference (RNAi) or post-transcriptional gene silencing (PTGS), which describes a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). The use of RNAi can involve the introduction of long dsRNA (e.g., greater than 50 bps) or siRNAs (e.g., 12 to 23 bps) that have complementarity to the target gene, both of which can be processed by endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

It would be appreciated that a cell line as described herein can be made deficient for more than one miRNA. For example, in some embodiments, a cell line can be made deficient for at least two or more miRNAs using mutagenesis and/or one or more transgenes. For example, one or more transgenes can be introduced into a cell that encode one or more inhibitory nucleic acids directed toward the same or different miRNAs.

A representative miR-21 knockout cell line was deposited with the American Type Culture Collection (ATCC; 10801 University Blvd., Manassas, Va., 20110) on Apr. 30, 2019 and assigned ATCC Deposit No. PTA-125918. This deposit will be maintained in the ATCC Depository, which is a public depository, for a period of 30 years, or 5 years after the most recent request, or for the enforceable life of the patent, whichever is longer, and will be replaced if it becomes nonviable during that period. The deposit of this material does not waive any infringement of the rights granted under this patent.

The methods described herein also can be used to provide gain-of-function to a cell line lacking a particular miRNA. For example, targeting a virus (e.g., an influenza virus) with a universally expressed miRNA also can be used for molecular biocontainment in cell culture experiments, helping to minimize the risk of the virus spreading to either mammalian or avian species. The system described herein can be used, for example, to safely test replication kinetics, cellular tropism, and/or therapeutic drugs in vitro against emerging strains of viruses.

Viruses Modified to Include a miRNA-Recognition Sequence

A miRNA-mediated vaccine platform as described herein also requires a modified virus. A modified virus as described herein includes at least one nucleic acid sequence in its genome that is recognized by at least one miRNA (referred to herein as a "miRNA-recognition nucleic acid sequence," sometimes referred to as a "miRNA target sequence"). Modified viruses as described herein can be made using materials and methods that are well known and routine in the art.

miRNA-recognition sequences would be understood to be a nucleic acid sequence, usually associated with a protein-encoding gene, to which a miRNA nucleic acid binds and directs their post-transcriptional repression. Therefore, a miRNA-recognition nucleic acid sequence typically is complementary to at least a portion of the mature strand of the miRNA (e.g., the strand that is loaded into the RNA-induced silencing complex). Bartel (2009, Cell, 136(2):215-33), incorporated by reference in its entirety, provides a detailed description of miRNA-recognition sequences and how they can be identified. As described herein, the miRNA-21 recognition sequence is TCA ACA TCA GTC TGA TAA GCT A (SEQ ID NO:14).

As with the knock-out cell lines, it would be appreciated that a modified virus can contain one miRNA-recognition nucleic acid sequence or a plurality of miRNA-recognition nucleic acid sequences. A plurality of miRNA-recognition nucleic acid sequence can include two, three, four, or more miRNA-recognition nucleic acid sequences. A plurality of miRNA-recognition sequences can be the same or different recognition sequences for the same miRNA and/or a plurality of miRNA-recognition sequences can be recognition sequences for a plurality of miRNAs.

As described herein, a skilled artisan can determine a suitable insertion site for the miRNA recognition sequence within the virus. It would be understood that insertion of the miRNA recognition sequence within the virus should have little to no effect on essential viral processes including, without limitation, replication of the virus, packaging of the virus, and/or interaction with essential host genes. In some instances, the miRNA recognition sequence can be introduced into a coding sequence of the virus (e.g., as described herein, in the NA sequence); in some instances, the miRNA recognition sequence can be introduced downstream of the stop codon of a coding sequence, so as not to disrupt the functionality of the coding sequence.

The modified viruses described herein (e.g., viruses containing at least one miRNA recognition nucleic acid sequence) can be attenuated further using other methods of attenuation (e.g., cold-adapted methods, temperature-sensitive).

Nucleic Acids

Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides between the two nucleic acids is determined. The number of identical matches is divided by the length of the aligned region (i.e., the number of aligned nucleotides) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid sequences to be carried out across their entire length (global alignment). Chenna et al., 2003, Nucleic Acids Res., 31(13):3497-500. ClustalW calculates the best match between a query and one or more subject nucleic acid sequences, and aligns them so that identities, similarities and differences can be determined. Gaps of one or more nucleotides can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

Methods of Making and Using a Live, Attenuated Virus

The cell lines described herein that are deficient in one or more miRNAs can be infected (e.g., transfected) with a modified virus as described herein and used to make live, attenuated viruses, which can be used as vaccines. The relationship that is required between the deficient miRNA(s) in the cell line and the miRNA-recognition nucleic acid sequence would be appreciated by a skilled artisan. That is, the miRNA(s) that are deficient in the knock-out cell line would, in the absence of the deficiency (e.g., in the absence of a mutation(s) or a transgene(s)), recognize the miRNA-recognition nucleic acid sequence that is contained within the modified virus.

The virus cultured can be collected and purified. Viruses can be collected and purified using any number of means and typically includes at least one cell culturing step in a suitable host cell or organism. See, for example, Acheson, 2011, Fundamentals of Molecular Virology, $2^{nd}$ Ed., Wiley & Sons.

A live, attenuated virus vaccine made by the methods described herein can be used to vaccinate a subject. The vaccination of a subject is routine in the art and typically includes inoculating the subject with the vaccine. Inoculation can be orally, rectally, topically, nasally, ocularly, intestinally, parenterally, or via the pulmonary tract. Routes of parenteral inoculation include intravenous, intramuscular, intradermal and subcutaneous administration. It would be appreciated that the live virus vaccine as described herein is attenuated in cells expressing the miRNA(s) (i.e., cells in the subject).

The methods described herein can be used as a platform to generate safe and effective vaccines in any number of subjects. For example, subjects can include mammals (e.g., humans, cattle, swine, ferrets, canines and felines) and avian species (e.g., domestic poultry species such as chickens, turkeys, and ducks).

The platform described herein can be used to produce live, attenuated virus vaccines using virtually any virus. The viruses that can be attenuated using the methods described herein include, without limitation, RNA and DNA viruses, and single-stranded and double-stranded viruses. Non-limiting examples of viruses that can be attenuated using the methods described herein include influenza virus (e.g., Influenza B virus; e.g., H1N1, H2N2, H3N2, H5N1, H5N2, H7N9, and H9N9), respiratory syncytial virus (RSV), polio virus, West Nile virus, Chikungunya virus, Ebola virus, Lassa virus, Dengue virus, SARS coronavirus, and Middle East Respiratory Syndrome (MERS) coronavirus.

It would be appreciated by a skilled artisan that the cell line that is made deficient for one or more miRNAs is limited only by the corresponding virus. That is, the cell line that is made deficient for one or more miRNAs needs to support the complete life cycle of the virus and needs to be able to produce new virions. Cell lines as used herein can be, for example, human pulmonary epithelial cells (A549), canine kidney cells (MDCK), or African green monkey kidney cells (Vero).

Articles of Manufacture

This disclosure also provides for articles of manufacture (e.g., "kits") that contain a live, attenuated virus as described herein. An article of manufacture also can include a corresponding knock-out cell line (e.g., in culture, lyophilized). Additionally, an article of manufacture may further include one or more buffers, adjuvants, or co-factors.

In some embodiments, an article of manufacture can include one or more syringes for delivering a live, attenuated virus as described herein to an individual (e.g., to vaccinate an individual). In some embodiments, a live, attenuated virus can be provided (e.g., packaged) within one or more syringes.

The components of an article of manufacture can be packaged together with suitable packaging materials. Articles of manufacture also can contain a package insert or package label having instructions thereon for using the live, attenuated virus and/or the knock-out cell line.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A—microRNA-Based Platform to Generate Live Viruses Attenuated Across Species Example 1—Small RNA Deep Sequencing microRNAs (miRNAs) were sequenced on the Illumina platform as previously described (Shapiro et al., 2010, RNA 16:2068-74; Pfeffer et al., 2005, Nat Methods, 2:269-76; and Langlois et al., 2013, Nature Biotech., 31:844-7). Briefly, RNA was extracted from the indicated tissue using standard TRIZOL protocols. RNA was run on a 15% denaturing Tris-Urea gel flanked by radiolabeled Decade markers (Ambion). Small RNA species between 15 and 30 nucleotides then were isolated, and the 3' end of the small RNA fraction was ligated to an adapter using the Rnl2 Air™ Ligase (BIOO Scientific). The resulting ligated RNA then was separated from the unligated adapters by gel purification using size to discriminate. The 5' end then was ligated to an adapter RNA oligonucleotide using T4 RNA ligase (NEB).

Following gel isolation, the ligation product was reverse transcribed, PCR amplified (21 cycles) and purified by agarose-based gel electrophoresis. Quality of the small RNA library was assessed on the Agilent 2100 Bioanalyzer (Agilent). RNA libraries were sequenced on the Illumina Platform and mapped to pre-miRNAs as annotated on miRBase (mirbase.org on the World Wide Web). Percent of total was calculated by dividing the indicated miRNA species by the total number of miRBase mapped small RNAs in the library. Families of miRNAs were pooled (e.g., miR-29a, miR-29b-1, miR-29b-2 and miR-29c-1 and miR-29c-2 were combined and designated "miR-29"), since there is a high level of conservation amongst the mature miRNAs produced from families.

Table 1 shows the results from the experiments described herein as well as data provided by Perez et al. (2009, Nature Biotechnol., 27:572-6), Langlois et al. (2012, Mol. Therapy, 20:367-75), Langlois et al. (2012, PNAS, 109:12117-22), and Langlois et al. (2013, Nature Biotechnol., 31:844-7). Table 1 is a heat map showing the amount of various miRNAs (% of total) in humans (A549 cells), ferret (respiratory tract; combined data for nasal, trachea, bronchus and lung parenchyma), canine (MDCK cells), mouse (embryonic fibroblasts), and chicken (embryonic tissue). Table 1 shows that, while there is some heterogeneity in miRNA expression across species, there are several miRNAs that are highly expressed across both species and cell types. Importantly, these miRNAs are expressed in species that are susceptible to influenza virus infection.

TABLE 1

Percent of miRNA Expression

|  | Human | Ferret | Canine | Mouse | Chicken |
| --- | --- | --- | --- | --- | --- |
| miR-21 | 43.0 | 2.9 | 38.8 | 10.3 | 2.8 |
| miR-24 | 6 | 3.2 | 3.8 | 3.2 | 11.6 |
| miR-23 | 3.1 | 3.0 | 2.5 | 0.6 | 3.1 |
| miR-103 | 1.4 | 0.3 | 3.2 | 1.3 | 3.1 |
| miR-29 | 6.0 | 1.6 | 4.6 | 6.9 | 1.0 |
| miR-31 | 6.0 | 0 | 5.2 | 5.0 | 0.1 |
| miR-125 | 1.8 | 3.8 | 1.7 | 0.7 | 0 |

Example 2—Western Blotting

The indicated MDCK cells were infected with wild type control or targeted influenza viruses at a multiplicity of infection of one. 24 hours post-infection, protein was harvested using a NP40 lysis buffer and run on a 4-15% gradient gel (BioRad). Protein was transferred to nitrocellulose blocked in 5% milk and probed using anti mouse NP antibody (NR43899 Bei resources) or anti sera from H7 HA immunized mice (gift from Dr. Peter Palese and Dr. Rong Hai, MSSM). Actin (anti mouse Pan Actin; Neomarkers) was used as a loading control. Protein was then revealed using anti mouse secondary antibodies conjugated to HRP (Roche).

Figure 2A:
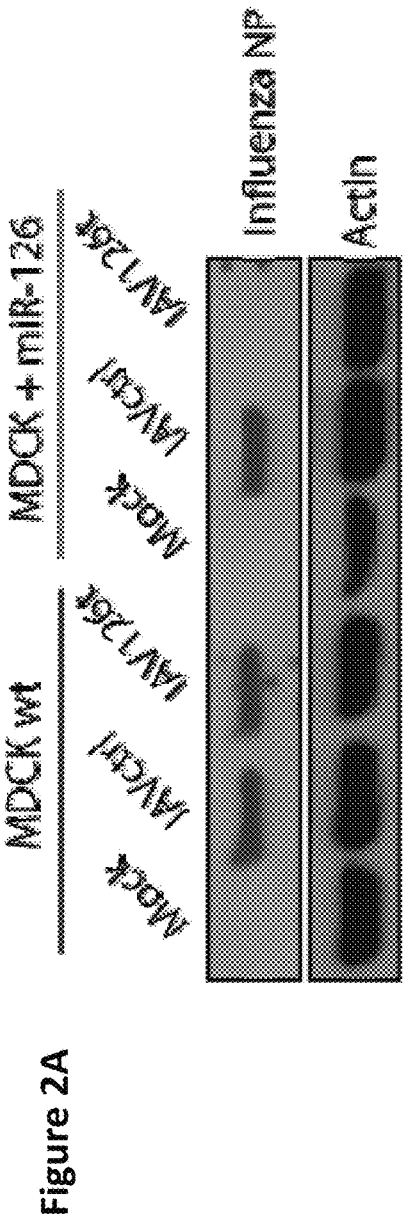
FIG. 2A is a photograph of a gel showing microRNA-mediated attenuation.
Figure 2B:
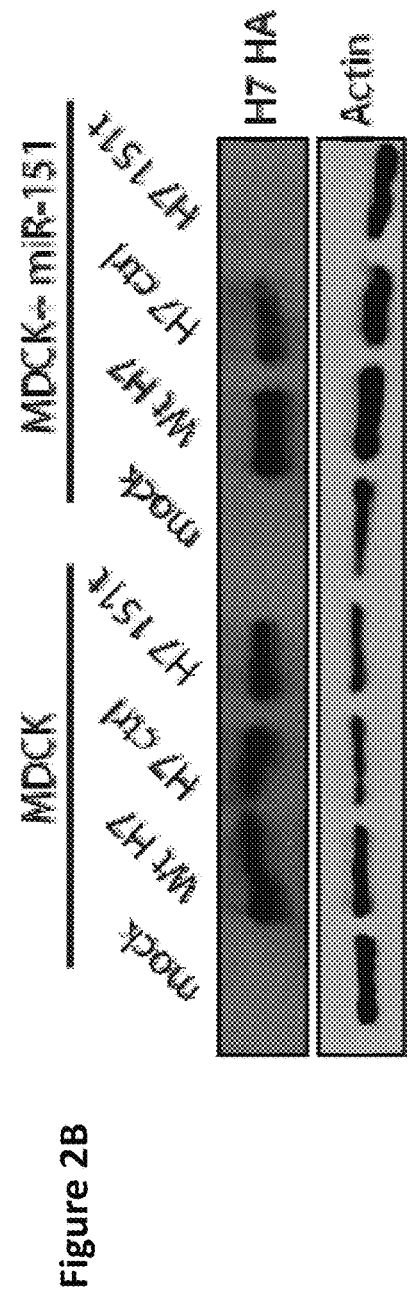
FIG. 2B is a photograph of a gel showing miRNA-mediated attenuation.
Figure 3A:
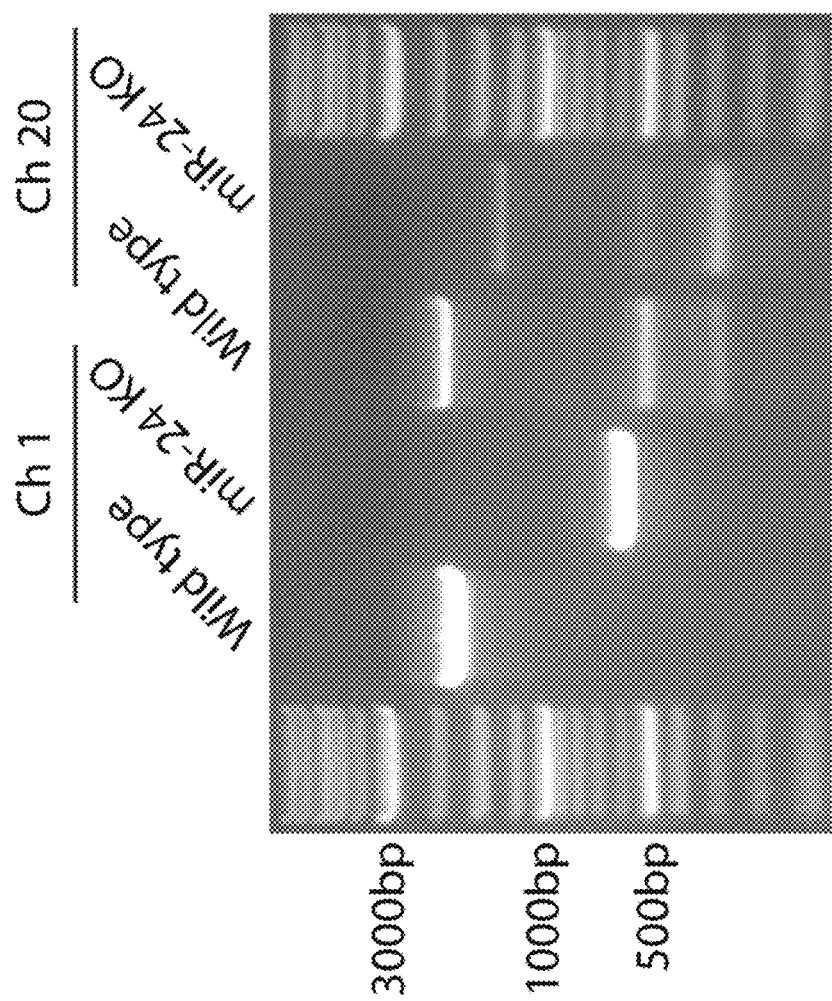
FIG. 3A shows CRISPR/Cas-mediated deletion of miR-24 from both loci in chromosomes 1 and 20 in MDCK cells. PCR primers specific for each miR-24 location were used and run on an agarose gel demonstrating deletion of miR-24.
Figure 3B:
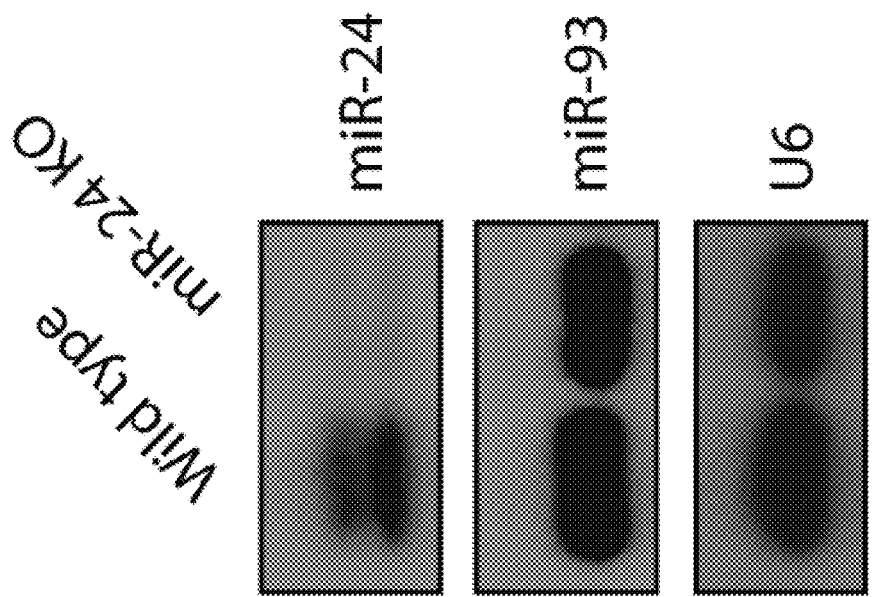
FIG. 3B is a RNA Northern Blot analysis from cells in FIG. 3A that demonstrates loss of miR-24 RNA expression.

The Western blots are shown in FIG. 2. MDCK cells lacking miR-126 (FIG. 2A) and miR-151 (FIG. 2B) were engineered to express these miRNAs. Influenza viruses were then generated with miR-126 recognition sites (CGC AUU AUU ACU CAC GGU ACG A (SEQ ID NO:1)) incorporated into NP (FIG. 2A) or miR-151 recognition sites (ACU AGA CUG UGA GCU CCU CGA (SEQ ID NO:2)) incorporated into H7 HA (FIG. 2B) (see Example 3 below). Wild type MDCK or miRNA-expressing MDCK cells were then infected and probed for targeted protein production. FIGS. 2A and 2B show that insertion of miRNA recognition sites in either the NP or the HA gene resulted in attenuated virus replication in the presence of the cognate miRNA but not in the absence of the cognate miRNA.

Example 3—Generation of Recombinant miRNA-Targeted Influenza Viruses miRNA-targeted recombinant influenza viruses were generated using the eight plasmid standard reverse genetics system (Fodor et al., 1999, J. Virol., 73:9679-82; and Langlois et al., 2013, Nature Biotech., 31:844-7). Four perfectly complementary recognition sites were cloned using overlapping PCR or synthesized by Genewiz. To allow for insertion into the influenza genome without disrupting the coding sequence of the protein or the packaging signals of the viral RNA, the complete packaging signal 200 base pairs from the 5' end of the vRNA was duplicated and added at the end of the stop codon. A unique restriction site was added, allowing for insertion of the targeting sequence using infusion cloning systems (Clontech). The targeted plasmid was then used with 7 plasmids from unmanipulated segments to rescue virus in 293 cells. Virus was then plaque purified and amplified in 10-day old embryonated chicken eggs.

Example 4—Generation of miRNA Knock-Out Cells miRNA knockout cells are generated by designing and transfecting guide RNAs flanking the 5' and 3' ends of the primary miRNA in the genome. Cells are co-transfected with a plasmid expressing the nuclease as well as the cognate miRNA-targeted virus. Cells are clonally selected and the loss of miRNA locus is confirmed by PCR and small RNA Northern blot analysis. MicroRNA targeted virus is inserted after the stop codon and upstream of a complete packaging signal. These viruses then are rescued and amplified in the miRNA knockout cell lines.

Part B—microRNA-21-Based Attenuation of Influenza Virus Across Susceptible Hosts

Example 5—Plasmid Construction

Modified A/Puerto Rico/8/1934 H1N1 (PR8) IAV gene segments were generated as previously described (Langlois et al., 2013, Nat. Biotechnol., 31:844-7; Langlois et al., 2012, PNAS USA, 109:12117-22). Briefly, the size of the duplicated 3' vRNA packaging sequence for each virus was 150 bp, except for NP viruses which contained a 200 bp duplicated packaging sequence. A unique restriction site was generated between the stop codon and the duplicated packaging sequence to insert four copies of miR-142 (5'-TCC ATA AAG TAG GAA ACA CTA CA-3' (SEQ ID NO:3)), miR-21 (5'-TCA ACA TCA GTC TGA TAA GCT A-3' (SEQ ID NO:4)) or scrambled control (5'-GCA AGC TGA CCC TGA AGT TCA-3' (SEQ ID NO:5)) target sequences (ctrl). Note there is a single G to A mutation outside of the seed sequence in 1 of 4 targets sites in the NA 21t segment.

Example 6—Cell Culture and Plaque Assays

Madin-Darby Canine Kidney (MDCK) (ATCC), A549 (ATCC), DF-1 (kind gift from Dr. Randy Albrecht and Dr. Adolfo Garcia-Sastre, Mount Sinai), 293T (ATCC) and MDCK 142(13) cells were maintained in Dulbecco's Modified Eagle Medium (DMEM) with 10% FBS and 1% pen/strep. MDCK 142 cells were supplemented with 1 mg/mL G418. Infections were carried out in infection media (PBS with 10% Ca/Mg, 1% pen/strep, 5% BSA) at 37° C. for one hour. Infection media was then replaced with an agar overlay (MEM, 1 mg/mL TPCK trypsin, 1% DEAE-dextran, 5% $NaCO_3$, 2% agar) and cells were cultured at 37° C. for 40 hours and then fixed with 4% formaldehyde. Blocking and immunostaining were done for one hour at 25° C. in 5% milk using the following antibodies: polyclonal anti-IAV PR8/34, 1:5000 (V301-511-552), Peroxidase Rabbit Anti-Chicken IgG, 1:5000 (303-035-003, Jackson Immuno Research). TrueBlue Peroxidase Substrate (50-647-28, Kirkegard & Perry Laboratories) was used as directed for detection of virus plaques.

Example 7—Generation of miR-21 KO MDCK Cells gRNA sequences were generated using GenScript's Interactive CRISPR gRNA design tool. gRNA oligos were phosphorylated and annealed prior to being ligated into BsmBI cut guide vector. The following gRNA's were used: 5' guide (upstream of miR-21 locus): TGA TAA GCT ACC CGA CAA GG (SEQ ID NO:6), 3' guide (downstream of miR-21 locus): ATC CCA AAG TCA AAC CTA GT (SEQ ID NO:7). All CRISPR/Cas9 associated cloning was performed as per the GeCKO Lentiviral CRISPR Toolbox protocol. Transfections were performed using Lipofectamine LTX with Plus Reagent as per manufacturer's instructions (Thermo Fisher Scientific). Cells were transfected with 500 ng of each gRNA plasmid, as well as a Cas9 expressing plasmid, Piggyback Puro R plasmid containing a transposable puromycin resistance gene, a Piggyback transposase plasmid (for co-transposition enrichment), and a control plasmid which expresses GFP using a previously published strategy (Moriarity et al., 2014, PLoS One, 9:e96114). Cells were selected with media containing 4 μg/mL puromycin and individual clones were isolated. For genotyping, cellular genomic DNA was extracted and PCR amplified using primers that flanked the two cleavage sites (F: 5'-GGT TGG TGT CTC ATG AAT GAG CT-3' (SEQ ID NO:8) and R: 5'-CCA CGA AAA TTT AAG GCA CAA AAT G-3' (SEQ ID NO:9)).

Example 8—Virus Rescue

Viruses were rescued in 293T cells by plasmid based transfection with the pDZ vector using methods previously described (Fodor et al., 1999, J. Virol., 73:9679-82; Hoffmann et al., 2000, PNAS USA, 97:6108-13). All miR-21 targeted virus rescues were supplemented with a plasmid encoding only mRNA for the corresponding targeted gene segment(s) to help offset the effects of miR-21 targeting in 293T cells. miR-21 targeted viruses were amplified in miR-21 KO MDCK cells. Viruses were sequence confirmed, and quantified by plaque assay (Langlois et al., 2012, PNAS USA, 109:12117-22).

Example 9—Small RNA Northern Blot

A549 and MLE15 cells in culture were infected with PR8 at a MOI of 1 and harvested at 24 hours post infection (hpi). A C57BL/6 mouse was infected with 40 pfu of PR8 and lungs were harvested at 24 hpi. RNA from cultured cells and mouse lungs were extracted using Trizol. RNA was separated on a 15% bis-acrylamide gel and transferred to hybond VX membrane. RNA was then crosslinked and detected with $P^{32}$ labeled probes. Probes included: anti-miR-21: 5'-TCA ACA TCA GTC TGA TAA GCT A-3' (SEQ ID NO:10), anti-miR-29a: 5'-TAA CCG ATT TCA GAT GGT GCT A-3' (SEQ ID NO:11), and anti-U6: 5'-GCC ATG CTA ATC TTC TCT GTA TC-3' (SEQ ID NO:12). miR-21 KO MDCK cell lines were also subjected to small RNA Northern blot as previously described (Langlois et al., 2012, Mol. Ther., 20:367-75; Pall and Hamilton, 2008, Nat. Protoc., 3:1077-84).

Example 10—Multicycle Growth Curve Analysis

Infections were carried out at a MOI of 0.02 in 1 mL of infection media for 1 hour at 37° C. Infection media was replaced with 2.5 mL viral growth media (DMEM with 1% pen/strep, 5% BSA) with 2 μg/mL TPCK trypsin for unmodified MDCK and miR-21 KO MDCK cells. For DF-1 cells, 0.7 μg/mL of TPCK trypsin was used. Supernatant was then collected at 0, 12, 24, 48, and 72 hpi and stored at −80° C.

Example 11—Western Blot

Infections were carried out at a MOI of 0.5 in infection media at 37° C. for one hour. Protein was harvested at 18-20 hpi and separated on a 15% SDS-PAGE gel (Bio-Rad). Separated protein was then transferred to nitrocellulose for two hours at 4° C. and membrane was blocked in 5% milk for 1 hour at 25° C. All subsequent staining was done in 5% milk at 4° C. for two hours using the following antibodies: monoclonal anti-IAV NP, clone IC5-1B7, 1:1000 (NR 43899, bei Resources), monoclonal anti-pan actin, clone ACTN05, 1:5000 (MS-1295-P, Thermoscientific), monoclonal anti-mouse IgG peroxidase-linked secondary antibody, 1:5000 (45-001-275, GE Healthcare), and monoclonal anti-IAV N1 NA, clone 4A5, 1:5000 (kind gift from Drs. Peter Palese and Gene Tan, Mount Sinai). Immobilon Western Chemiluminescent HRP substrate (WBKLS0500, EMD Millipore) was used for protein detection as directed. Re-Blot Plus Strong Solution (10×) was used as needed for stripping (2504, EMD Millipore). Blots were visualized using the Li-Cor Odysssey Fc imaging system.

Example 12—Mice and Virus Infection

C57BL/6 mice were purchased from The Jackson Laboratory. Mice were anesthetized using a weight-based dose of ketamine/xylazine, which was delivered intraperitoneally. Mice were infected intranasally (i.n.) with 100 pfu unless otherwise indicated. Inactivated virus was generated through 20 minutes of UV exposure at room temperature. Lungs were harvested at 3 days post infection (dpi) and homogenized in PBS for analysis of virus titer in MDCK cells. During infection, all mice having weight loss exceeding 25% of their initial starting weight were sacrificed. All experiments involving mice were performed as dictated by the University of Minnesota Institutional Animal Care and Use Committee.

Example 13—Hemagglutination Inhibition Assay

Cheek bleeds were performed on mice at 28 dpi. Blood was stored at 25° C. for one hour and then spun at 3000 rpm (1500× G) for 15 minutes at 4° C. with no break. Serum was then treated with Receptor Destroying Enzyme (RDE) of *Vibrio cholera* filtrate (Sigma, C8772) overnight at 37° C. and then inactivated using 2.5% sodium citrate at 56° C. for 30 minutes. Serum was then serially diluted 1:2 out to 1:2048. Serum was incubated with 8HAU/50 ul of PR8 virus for 30 minutes at 25° C. 0.5% chicken red blood cells were then added to each well and stored at 4° C. for 45 minutes at which point wells were checked for hemagglutination.

Example 14—Statistics

Statistical analysis was executed using GraphPad Prism 7 software. Comparisons between two groups were performed using a two-tailed Student t test, and $p<0.05$ was considered statistically significant. Error bars are calculated using standard deviation.

Example 15—miRNA Silencing of Individual IAV Gene Segments Demonstrates Variable Attenuation Previously, miRNAs were used to target IAV NP and HA mRNAs, which demonstrated differential levels of attenuation (Langlois et al., 2013, Nat. Biotechnol., 31:844-7; Langlois et al., 2012, PNAS USA, 109:12117-22). However, the use of different miRNAs makes it difficult to directly compare the effects of targeting these gene segments. Additionally, the level of attenuation associated with miRNA targeting of each individual IAV gene segment has never been determined. Therefore, an analysis was carried out to systematically determine which viral gene segments yielded the greatest attenuation by miRNAs. miRNA silencing was assessed using the hematopoietic-specific miR-142 as a model because it has been previously shown to strongly repress targeted foreign transcripts, including IAV mRNA (Langlois et al., 2012, PNAS USA, 109:12117-22). This could then inform future studies looking at segment-specific targeting. Recombinant viruses were generated containing four perfect miR-142 target sites (gene-142t) or an equivalent length of control target sites (gene-ctrl) after the stop codon followed by a complete packaging signal on the 5' end of the vRNA. Each of the six unspliced gene segments encoding a single protein were individually targeted while leaving the remaining seven segments unmodified. To measure the effect of miRNA silencing on viral replication, each targeted virus and its corresponding control virus were grown in unmodified MDCK cells, which lack miR-142, and MDCK cells engineered to express miR-142 (MDCK142). Significant attenuation of NP-142t virus was observed in MDCK142 cells, with a three to four log reduction in viral titer as compared to replication in MDCK cells (FIG. 4A). Significant attenuation was also observed when the miR-21 recognition sequence was placed within the polymerase basic 2 (PB2) viral sequence, the polymerase basic 1 (PB1) viral sequence, the acid polymerase (PA) viral sequence, and the hemagglutinin (HA) viral sequence targeted viruses although to a lesser extent than when placed within the nucleoprotein (NP) viral sequence, with a single log reduction or less in viral titer under silencing conditions (FIG. 4B-4E). NA targeted virus showed similar replication kinetics in both MDCK142 and MDCK cells (FIG. 4F). Importantly, this was not a result of lack of targeting, as NA protein levels were reduced in the targeted virus in the presence of the cognate miRNA (FIG. 4F, inset). As expected, the corresponding control viruses showed similar levels of replication in both MDCK and MDCK142 cells. These data suggest that miRNA silencing of IAV NP most effectively blunts viral replication. Furthermore, the variable level of attenuation observed with segment-specific miRNA silencing suggests that targeting of multiple gene segments could be used to customize viral attenuation and potentially prevent reassortment.

Example 16—miR-21 is Abundantly Expressed in IAV Susceptible Hosts and its Expression is Unaffected by IAV Infection Previously, through deep sequencing, expression of miR-21 was demonstrated in human, chicken, ferret, and canine cells ((Langlois et al., 2013, Nat. Biotechnol., 31:844-7; Langlois et al., 2012, PNAS USA, 109:12117-22; Perez et al., 2009, Nat. Biotechnol., 27:572-6). Additional studies also have demonstrated that miR-21 is ubiquitously expressed across cell types and tissues in mammals and birds (Landgraf et al., 2007, Cell, 129:1401-14; Xu et al., 2006, FEBS Lett., 580:3610-6). To ensure that miR-21 is a suitable miRNA for use in the system described herein, expression in IAV susceptible hosts was confirmed by small RNA Northern blot analysis. Cell lines derived from canine (MDCK), chicken (DF-1), human (A549) and mouse (MLE15) origin showed strong expression of miR-21 (FIG. 5A). Production of the miRNA in cultured cells and in mouse lungs in vivo was unaltered by infection with IAV (FIGS. 5B and 5C). Together, these data demonstrate the broad expression of miR-21, making it an ideal candidate for use as a miRNA to target and attenuate replication in IAV susceptible hosts.

Example 17—Engineering of miR-21 Targeted Virus

Due to the ubiquitous expression of miR-21, it was necessary to engineer an in vitro platform lacking miR-21 for growth of the corresponding targeted viruses. In the *Canine familiaris* genome, miR-21 is expressed in a single location on chromosome nine (Hoeppner et al., 2014, PLoS One, 9:e91172). Therefore, guide RNAs upstream and downstream of the miR-21 locus were designed to completely excise the hairpin using CRISPR/Cas9 genomic editing with a predicted deletion of approximately 880 bp (FIG. 6A). Potential miR-21 knockout (miR-21 KO) MDCK cell clones were screened by PCR and compared to unmodified MDCK cells, which were expected to yield a band of 1750 bp. The miR-21 KO MDCK cell line resulted in a PCR product of approximately 870 bp indicating a deletion of the expected size (FIG. 6B). To further verify that miR-21 had been deleted, small RNA Northern blot analysis was performed and no detectable expression of miR-21 was observed in the knockout cells (FIG. 6C). Another ubiquitously expressed miRNA, miR-29a, was also probed to verify miR-21 was the specific target of gene editing. Similar expression of miR-29a in both the miR-21 KO MDCK cells and unmodified MDCK cells was observed (FIG. 6C). miR-21 KO MDCK cells demonstrated no growth or viability defects compared to unmodified MDCK cells.

Using the miR-21 KO cell line, a recombinant IAV was generated containing four perfect miR-21 target sites (TCA ACA TCA GTC TGA TAA GCT A (SEQ ID NO:14)) or control target sites in NP as targeting of this segment resulted in the most robust attenuation in our model system (FIG. 4A). To assess the efficacy of miR-21 silencing of viral mRNA, unmodified MDCK cells, which robustly express the cognate miRNA, and miR-21 KO MDCK cells were infected with either NP-21t or NP-ctrl viruses. Western blot analysis in MDCK cells infected with NP-21t virus showed complete knockdown of NP protein, whereas NP levels in miR-21 KO MDCK cells were similar to NP-ctrl virus in either cell type (FIG. 6D). To assess the effect of miR-21 silencing on replication, multicycle growth analysis was performed for NP-21t and NP-ctrl viruses in unmodified MDCK cells and miR-21 KO MDCK cells. A 1.5-3 log reduction in viral titer of NP-21t virus in unmodified MDCK cells was observed as compared to replication in miR-21 KO MDCK cells (FIG. 6E). As expected, NP-ctrl virus showed similar replication kinetics in both cell lines. These data indicate that miR-21 effectively targets viral mRNA resulting in significant attenuation.

Example 18—miR-21 Attenuates Targeted IAV in a Range of Species miR-21 silencing was determined in other IAV susceptible hosts. Infection of A549 cells in an in vitro model for human lung was assessed. In A549 cells infected with NP-21t virus, there was a complete loss of viral NP expression (FIG. 7A). To determine if miR-21 expressed in an avian host is capable of repressing targeted IAV replication, chicken fibroblast DF-1 cells were infected with NP-21t or NP-ctrl virus and multicycle growth analysis was performed. NP-21t virus showed over a two log reduction in titer compared to NP-ctrl virus grown in DF-1 cells (FIG. 7B). To assess miRNA silencing in an intact mammalian host, mice were infected with NP-21t or NP-ctrl viruses and viral growth was assessed by plaque assay at 3 dpi. In agreement with in vitro data, analysis of the lungs also demonstrated a selective block of NP-21t virus replication (FIG. 7C). Taken together, these data indicate successful miRNA silencing in mammalian and avian hosts.

Example 19—miR-21 Targeted Virus Provides Protective Immunity During Lethal Challenge Having verified significant attenuation in vitro and in vivo, it was next assessed whether vaccination with NP-21t virus induces a protective immune response. As a control for vaccination, a live-attenuated cold-adapted IAV (CA IAV) modified from the FDA approved vaccine for use in humans was used. This CA IAV is composed of the six internal genes from the cold-adapted A/Ann Arbor/6/60 H2N2 virus (Maassab, 1967, Nature, 213:612-4; Maassab, 1969, J. Immunol., 102:728-32) and the two external genes from PR8. Mice were infected with NP-21t virus or CA IAV and weight loss was measured over the first 12 dpi to assess vaccine safety. A higher inoculum of CA was used similar to what has been previously described (Chen et al., 2011, PNAS USA, 108:1140-5). As a control, mice also were vaccinated with UV killed NP-21t to confirm that protection is driven by attenuated replication rather than incoming virus particles alone. No significant weight loss was observed in any vaccinated or naïve mice (FIG. 8A). Expectedly, all mice survived to 28 dpi. To determine if these vaccines elicited IAV-specific antibodies, serum was analyzed by HA inhibition assay. These data demonstrate that both NP-21t and CA vaccines drive significant IAV-specific antibody responses (FIG. 8B). Conversely, UV killed vaccine failed to induce an IAV-specific antibody response, consistent with previous findings. At this time point, mice were challenged with a lethal dose of PR8. Within the first seven days post-challenge, all of the unvaccinated mice succumbed to the infection (FIG. 8C). All mice vaccinated with either NP-21t or CA IAV were protected during lethal challenge, demonstrating 100% survival and no significant weight loss (FIG. 8C). Importantly, the same dose of UV inactivated vaccine failed to protect, suggesting that attenuated replication is needed to drive protection (FIG. 8C). These data demonstrate that vaccination with NP-21t virus induces robust immunity and subsequent protection during secondary infection with a subtype matched IAV.

Example 20—miRNA Targeting of Multiple Gene Segments

To determine if the degree of miRNA-mediated attenuation could be varied, two IAV gene segments were targeted in tandem. A recombinant IAV containing four perfect miR-21 target sites or control target sites in the PA and NA gene segments (PA/NA-21t or PA/NA-ctrl, respectively) were generated. To assess the effects of miRNA silencing on virus replication, multicycle growth analysis was performed in miR-21 KO MDCK cells and unmodified MDCK cells. PA/NA-21t virus grown in MDCK cells showed a 2.5-3 log reduction in replication compared to growth in miR-21 KO MDCK cells (FIG. 9A). PA/NA-ctrl virus showed similar replication kinetics in both cell lines. As compared to NP-21t virus (see FIG. 6E), increased attenuation was observed when targeting both PA and NA gene segments. To further demonstrate the plasticity of miRNA targeting of IAV, a virus containing four perfect miR-21 target sites or control target sites in the PA and HA gene segments (PA/HA-21t or PA/HA-ctrl, respectively) was generated. This virus demonstrated significant attenuation in the presence of the cognate miRNA (FIG. 9B). However, targeting of PA and HA together appears to be less efficient than the PA and NA combination. Together, these data indicate that this proposed platform allows for customizable attenuation, potentially improving the safety and versatility of current vaccine platforms.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A cell culture of a miRNA-21 knockout cell line, the knockout cell line comprising a deletion of, or one or more mutations in, the endogenous miRNA-21 nucleic acid sequence.

2. The cell culture of claim 1, wherein the cell line is a eukaryotic cell line.

3. The cell culture of claim 1, wherein the cell line is a Madin-Darby Canine Kidney (MDCK) cell line.

4. The cell culture of claim 1, wherein the miRNA-21 has the sequence shown in SEQ ID NO:13.

5. The cell culture of claim 1, wherein the one or more mutations are selected from the group consisting of a deletion, an insertion, a point mutation, or a substitution.

* * * * *